United States Patent [19]

Kraus

[11] 4,421,115
[45] Dec. 20, 1983

[54] ELECTRIFICATION ATTACHMENT FOR AN OSTEOSYNTHESIS IMPLANTATE

[76] Inventor: Werner Kraus, Kaulbachstrasse 71, D-8000 München 22, Fed. Rep. of Germany

[21] Appl. No.: 214,099

[22] Filed: Dec. 8, 1980

Related U.S. Application Data

[62] Division of Ser. No. 944,917, Sep. 25, 1978, Pat. No. 4,306,564.

[30] Foreign Application Priority Data

Sep. 22, 1977 [DE] Fed. Rep. of Germany ....... 2742741

[51] Int. Cl.³ .............................................. A61N 1/18
[52] U.S. Cl. ................................. 128/419 F; 128/784
[58] Field of Search .................. 128/419 F, 82.1, 783, 128/784, 785, 799

[56] References Cited

U.S. PATENT DOCUMENTS

| | | | |
|---|---|---|---|
| 3,783,880 | 1/1974 | Kraus ................................ | 128/82.1 |
| 3,820,534 | 6/1974 | Kraus et al. ....................... | 128/82.1 |
| 3,890,953 | 6/1975 | Kraus et al. ...................... | 128/82.1 X |
| 3,915,151 | 10/1975 | Kraus ................................ | 128/82.1 |

Primary Examiner—Lee S. Cohen

Attorney, Agent, or Firm—Frishauf, Holtz, Goodman & Woodward

[57] ABSTRACT

To permit electric stimulation of tissue and specifically bone tissue to which an osteosynthesis plate or a bone nail has been attached, and provide electrical energy by induction from an external induction coil, a support body 22, 110, 222 is provided for attaching association with the osteosynthesis implantate; at least one induction coil 24, 118, 224 is embedded in, or secured to the body, electrodes 28, 36, 80, 118a, 228, 236 are connected to the windings of the coil, one of which is connectable with a conductive portion of the osteosynthesis implantate, the other electrode being exposed to bone tissue or soft tissue of the patient. When used in association with a hollow, slotted bone nail (FIGS. 1 to 6, 12 to 24), the implantate can be constructed as an elongated plastic rod which can be introduced into the bone nail, one electrode protruding therefrom and making contact with the bone nail, the rod being of plastic which can be cut to length to fit the length of the bone nail; when the implantate is a plate (FIGS. 9 to 11), the windings can be included in a strip arranged for slipping on and clamping around the edge of the plate, with projecting electrode connections.

18 Claims, 13 Drawing Figures

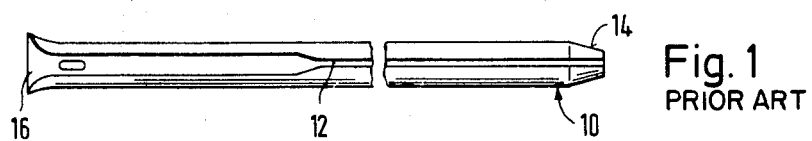
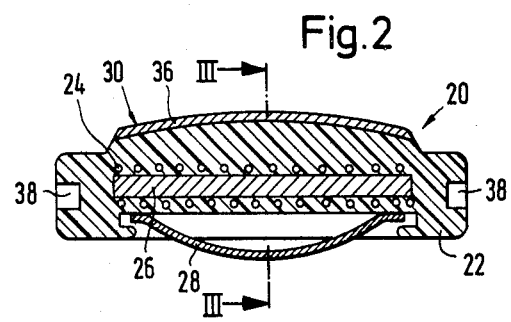 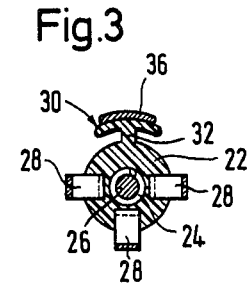
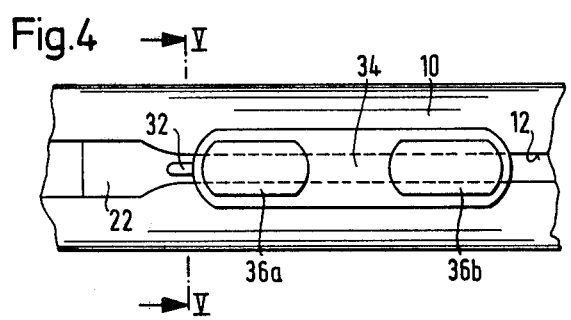 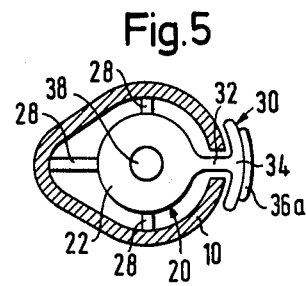
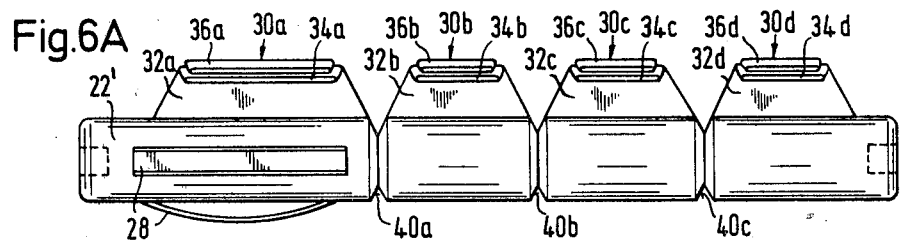
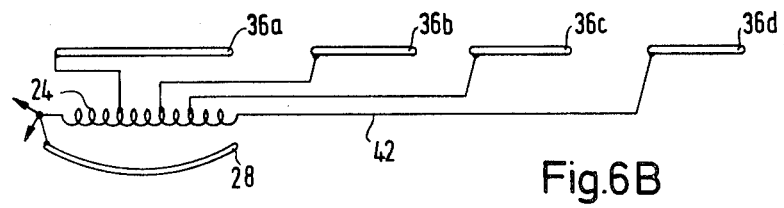

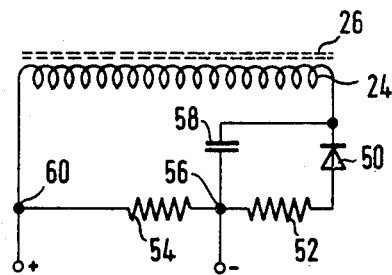
Fig.7
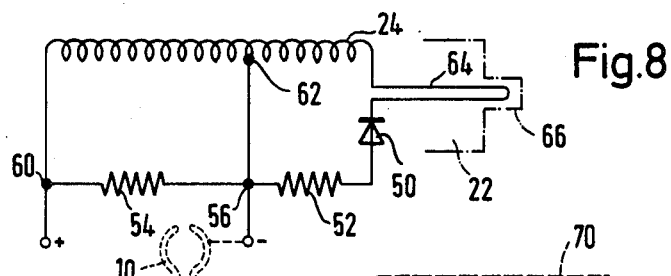
Fig.8
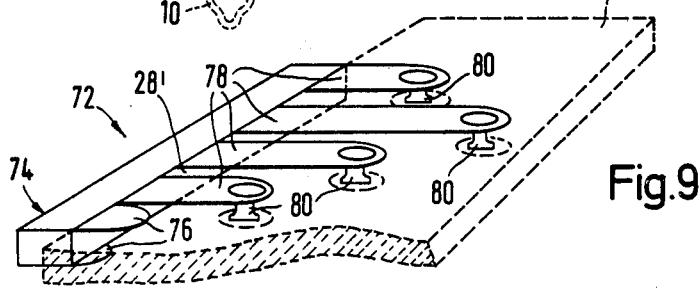
Fig.9
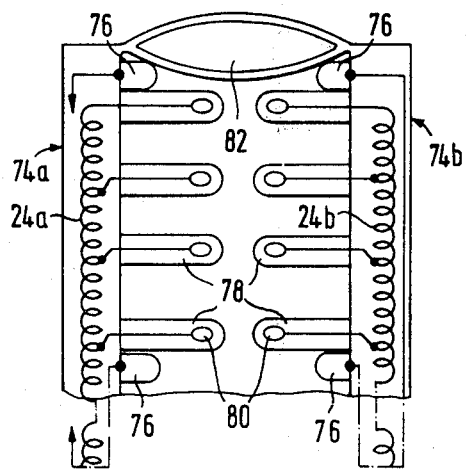
Fig.10
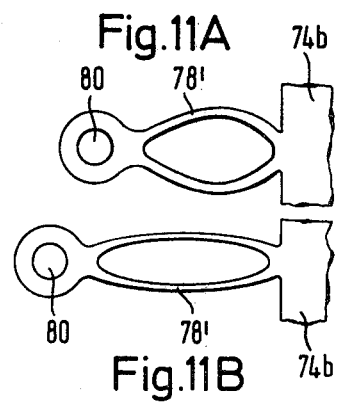
Fig.11A
Fig.11B

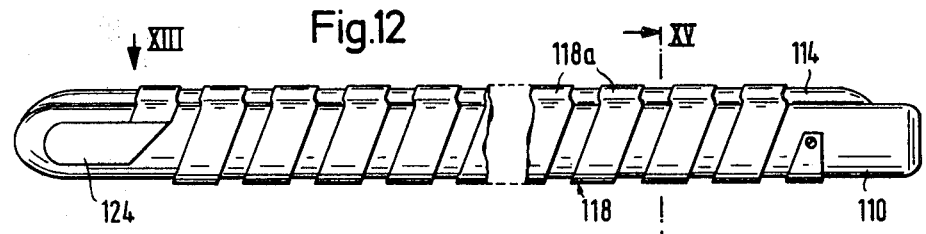
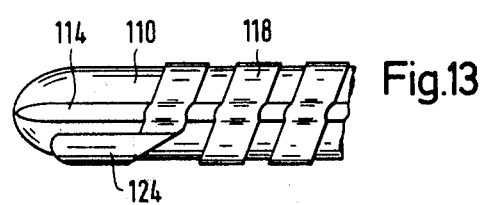
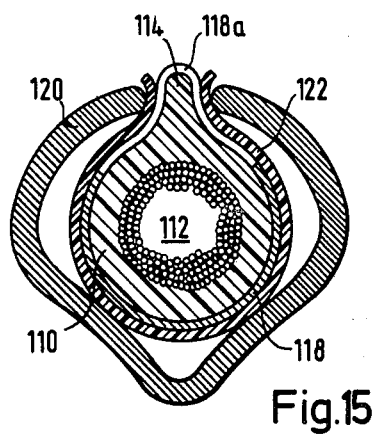
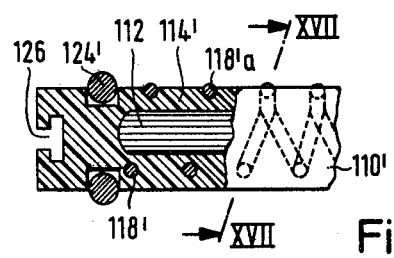
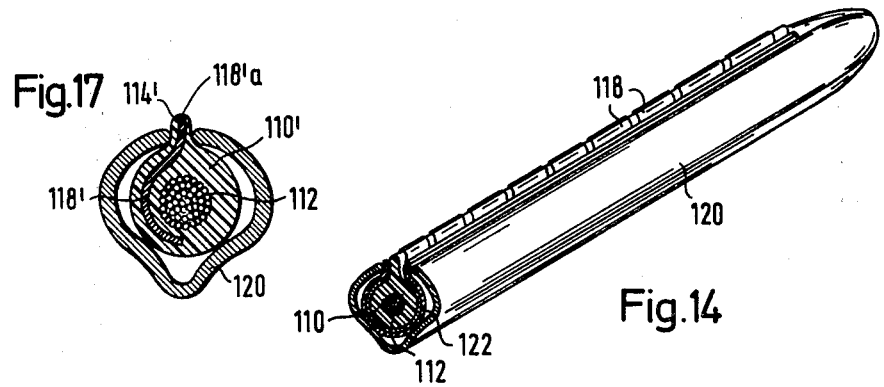
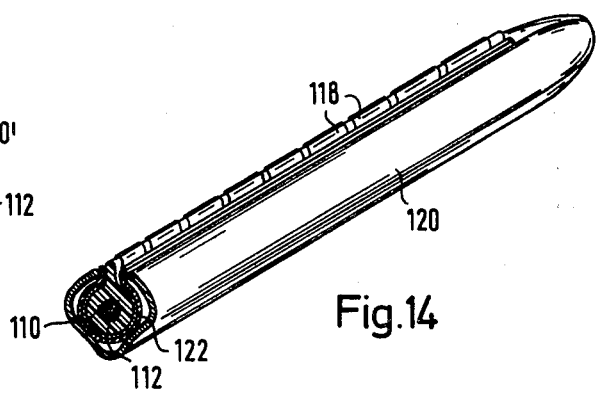
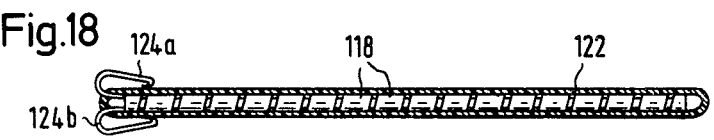

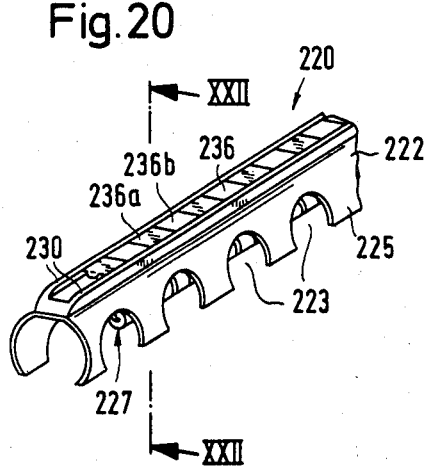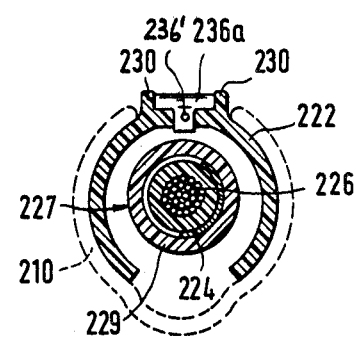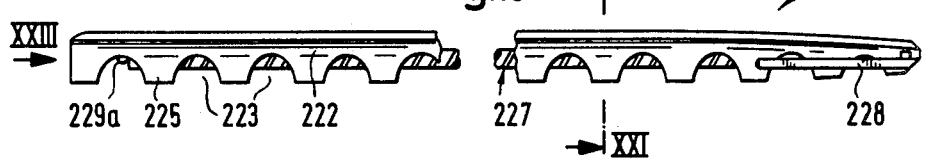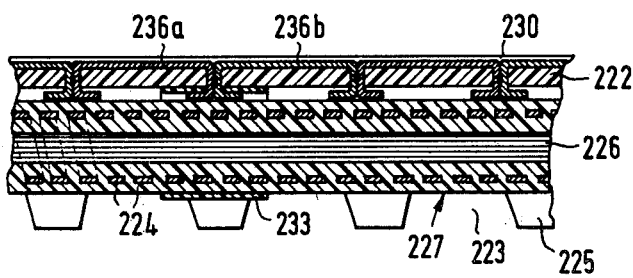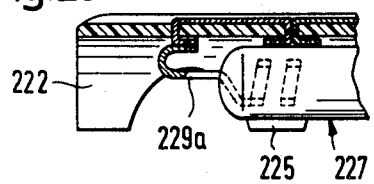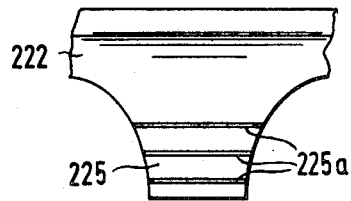

ELECTRIFICATION ATTACHMENT FOR AN OSTEOSYNTHESIS IMPLANTATE

This is a division of application Ser. no. 944,917 filed Sept. 25, 1978 now U.S. Pat. No. 4,306,564, issued Dec. 22, 1981.

REFERENCE TO RELATED PUBLICATIONS

U.S. Pat. No. 3,745,995 (corresponding: German Patent No. 19 18 229)

U.S. Pat. No. 3,820,534 (corresponding: Swiss Patent No. 551,201)

U.S. Pat. No. 3,918,440

German Disclosure Document DE-OS No. 23 11 817

The present invention relates to a surgical prosthesis, and more particularly to an osteosynthesis implantate, which, after its manufacture, can be associated with an electrical pick-up element to provide a small electrical voltage across the implantate and surrounding tissue of the patient to stimulate healing processes.

The term "tissue" as used herein includes soft tissue as well as bone tissue, unless it clearly appears otherwise.

BACKGROUND AND PRIOR ART

It has previously been proposed—see the referenced U.S. Pat. Nos. 3,745,995 and 3,820,534—to provide an inductive receiving coil, preferably having a ferromagnetic core, for association with osteosynthesis implantates. The receiving coil has two or more connecting terminals, connected to electrodes which are attached to an injured or damaged bone which is fixed in relative position by the osteosynthesis implantate. Such an implantate may, for example, be a bone nail, securing together the ends of a fractured bone by extending through the marrow duct. After the operation of introducing the bone nail, and of closing the wound, a low-frequency electrical current is induced in the coil which flows through the electrodes and the damaged bone region, and promotes healing and reformation of bone substance.

Such osteosynthesis implantates are known as electro-osteosynthesis implantates and are provided with the receiving coil and the electrode connections, as delivered from the manufacturer. The manufacture of any one electro-osteosynthesis implantate requires individual, special manufacture in which the electrical winding elements and the osteosynthesis implantate are individually associated. Such implantates may, also, be in the form of flat or bendable plates. The winding section is individually and securely connected to the implantate by adhesion, clamping connection or welding; likewise, the electrodes or electrode connection are so adhered or connected. Surgical clinics, trauma stations in hospitals, and the like, require a large stock of different types of electro-osteosynthesis implantates, for example bone nails of many different lengths in many different diameters. Such electro-osteosynthesis implantates are expensive and stocking and storage of a large number of such items in many different sizes, the requirements for which are hardly predictable, is a substantial drain on limited financial resources of public and private health facilities. Frequently, therefore, the patient is subjected to multiple surgical procedures since electro-osteosynthesis implantates were frequently introduced into the patients only in a second operation, after the initial operation of fixation of the bone has taken place, the type and size of the required electro-synthesis implantate has been determined and the appropriate unit has been ordered and received from the manufacturer.

Developments in surgical devices have been undertaken to reduce the financial load on health facilities and to reduce the requirement for stocking of specific electro-implantates. U.S. Pat. No. 3,820,534 describes a belt-like element which is furnished with electrodes and a connecting element on which a coil is secured. After implantation of a bone nail, for example, the belt-like element is placed around the bone, and the connecting coil can be connected to the bone nail with one terminal. It has also been proposed to provide a loose pick-up coil which is embedded in a biologically tissue-compatible plastic material and which can be connected to bone screws by means of snap-button type connections. The bone screws function as electrodes across which an electric current will flow (see German Disclosure Document DE-OS No. 23 11 817). U.S. Pat. No. 3,918,440 describes such a loose receiving coil in combination with bone screws, in which the head of the bone screws is insulated so that it can be used for attachment of a bone plate. The screws, themselves, form the electrodes which are insulated with respect to the bone plate.

The loosely implanted pick-up coil, as well as the belt-like element, and the snap button or push-button type connections are an entirely satisfactoy substitute for premanufactured electro-osteosynthesis implantates. Use of the belt-like element introduces additional complexity; the loose pick-up coil is difficult to secure.

THE INVENTION

It is an object to provide an attachment element for an ordinary osteosynthesis implantate, such as a bone plate, which can be applied to the implantate so that it can be converted into an electro-implantate during the progress of an operation and which then will be a fully equivalent and effective substitute for a premanufactured electro-implantate.

Briefly, in accordance with the invention, a support body is provided, formed for attaching association with the osteosynthesis implantate. The support body has at least one induction coil therein; when made for association with an osteosynthesis plate, it is formed with means to attach the body to the osteosynthesis plate, for example by a clamp or snap-over connection. At least two electrodes are brought out from the winding within the support body. One of the electrodes, which can be fixedly secured to the end of one of the windings, can be made to be connectable with the osteosynthesis implantate, for example by a spring element, or elements. The other electrode can also be secured to the body or otherwise brought out.

The attachment permits the surgeon to fix the bone in standard manner by an osteosynthesis implantate, for example by a plate in accordance with standard surgical procedure, and using the ordinarily available implantates. He can then determine whether it would be desirable to have an electrical implantate and, if so, the osteosynthesis plate or can be supplied with the attachment in accordance with the present invention and the implantate will then function as an electro-implantate without requiring any further changes or modifications, or a subsequent operation.

The attachment can be so made that it is universally acceptable by at least a group of bone nails having different diameters, as provided by manufacturers, determined, for example, by manufacturing or governmental standards (see, for example, German Industrial Standard DIN 55801).

A standard osteosynthesis implantate, in the form of a bone support plate, and the attachment in accordance with the present invention, together, are substantially simpler and further less expensive than the combined electro-osteosynthesis implantates.

Drawings, illustrating preferred examples, wherein:

FIG. 1 is a top view of a standard bone nail in accordance with German Industrial Standard DIN 55801, Form B;

FIG. 2 is a schematic simplified longitudinal section of an electrification attachment for the bone nail of FIG. 1, as generally claimed in parent U.S. Pat. No. 4,306,564;

FIG. 3 is a cross section in the plane of III—III of FIG. 2;

FIG. 4 is a top view of a bone nail of FIG. 1, partly in phantom view;

FIG. 5 is a cross section in plane V—V of FIG. 4;

FIG. 6 is a side view of a modified embodiment of the attachment of FIG. 2, in which the electrical circuit inherent in the element is separately shown in view B, and the structural arrangement is shown in view A;

FIGS. 7 and 8 are two schematic electrical diagrams suitable for use in the electrical attachment;

FIG. 9 is a highly schematic perspective view of an osteosynthesis plate, shown in broken lines, to which the electrification attachment in accordance with the present invention has been added;

FIG. 10 is a schematic top view of another arrangement of an osteosynthesis plate and;

FIG. 11 is a top view of an elastic electrode connection holding arrangement, in which view A illustrates the holding arrangement in relaxed state, and view B the same arrangement in stretched, or stressed state.

The invention will best be understood when considering first an embodiment for attachment to a standard bone nail, as shown in FIG. 1. The cross section of the bone nail of FIG. 1 is approximately clover leaf-shaped, or pear-shaped (FIG. 5). The bone nail 10 has a longitudinal slot 12, a tapering, somewhat pointed tip 14 and an enlarged terminal end 16.

In accordance with the present invention, the known and conventional bone nail 10 is converted into an electo-bone nail by the attachment 20—see FIGS. 2 and 3. Damaged or diseased or fractured bone tissue is electrodynamically stimulated in the region of injury or disease to stimulate reformation of bone tissue and improve and accelerate the healing process.

The attachment 20, in accordance with the present invention, has a body 22 made of a biologically compatible, tissue-compatible plastic, such as polyethylene, or a carbon-fluoropolymer. A receiving coil 24, shaped like a solenoid, is embedded in the body 22. The receiving coil 24 is only schematically shown in FIGS. 2 and 3, and there illustrated as a single-layer coil; of course, it may be a coil wound of a plurality of tightly arranged windings. The circuit and the electrical terminals having been omitted from the illustration of FIGS. 2 and 3 for simplicity, and will be explained below.

The coil 24 preferably is a cored coil, and has a magnetic core 26 made of a magnetically soft material, having soft-iron characteristics, such as a ferrite, or an iron-nickel alloy. It may also be a permanent-magnet material which, then, preferably, is brought into a partially saturated condition and permits modification of the wave shape of the voltage applied to the electrodes and hence of the currents being supplied to the body tissue.

Embodiment of FIGS. 2 and 3

The body 22 has three leaflike, spring electrodes 28 secured thereto, for example by being set into a groove of the body (see FIG. 2) which are bowed outwardly. The electrodes 28 are connected together and to one end terminal or end point of the winding 24 and provide electrical connection of the attachment to the metal bone nail 10, by bearing against the inside wall, as illustrated in FIG. 5. The dimensions of the body 22 and the outward bulge of the electrodes 28 are preferably so selected that the same attachment 20 can be used for bone nails of a wide range of diameters, preferably the entire range of diameters of bone nails which are used in surgical procedures. At most, however, two such bodies 20 need be provided, one for a thinner group of bone nails and another for a group of bone nails having a wider diameter. The spring electrodes 28 permit deflection, and hence reliable electrical contact, as well as reliable seating within the bone nail.

The body 22 is formed with an extension 30 which, in cross section, is essentially T-shaped (FIG. 3) and which fits through the slot 12 of the bone nail 10. The upper cross portion 34 of the T-extension 30 (FIG. 5) is bent downwardly so that it fits at least approximately around the curvature of the bone nail 12. Since the body 20, with the integral extension 30, is made of a soft plastic, the pre-bowing of the cross portion 34 can be such that it fits the thinnest nail, since it will then expand, or resiliently bow outwardly to fit over nails of larger diameter. In longitudinal extent, the cross portion 34 can be flat (FIGS. 4, 5) or can be slightly bowed (FIG. 2). An electrode 36 is applied to the outside of the bowed cross extension 34, connected to another point on the winding 24 of the attachment. The electrode 36 is the counter electrode or soft-tissue electrode of the attachment.

Embodiment of FIG. 4

A plurality of separate counter electrodes 36a, 36b can be provided, each one connected to different points on the winding of the coil 24. In all other respects, the structure is similar to that of the embodiment of FIGS. 2 and 3.

The body 22 is preferably formed at its end with recesses, notches or grooves 38 to permit attachment of an insertion or removal tool, and to facilitate insertion or removal of the attachment 20 into or from the nail 10.

In a preferred form, the surgeon is provided, together with the attachment 20, with an additional filler strip which, for example, may be formed similar to an I-beam, that is, have a double T-profile in cross section, and so dimensioned that it cannot pass through the narrow end 14 of the bone nail. The filler strip is then trimmed to the desired length by the surgeon during the operation and introduced into the nail 14 together with the attachment 20 in order to ensure proper spacing of the attachment 20 from the end 14 of the nail, or in order to ensure spacing between a plurality of attachment elements 20 which can be sequentially, axially introduced into the nail 10. The filler strip is preferably made of the same material as that of the body 20, and soft enough so that it can be cut by surgical scissors to the desired length, being supplied, for example, in coil or rod form.

The body 22 with the T-projection 30 and the electrode 36, or the electrodes 36a, 36b, are so dimensioned that they fit within the diameter of the surgical drill with which the opening for the bone nail 10 is drilled.

The entire length of the attachment 20 preferably is between about 3 to 5 cm. The material is somewhat resilient and the dimensions are preferably so arranged that, coupled with the elasticity of the material of the body 22, it is possible to introduce the attachment simply and effortlessly even over a bent-over end formed at the upper end of a bent bone nail and from there into the there widened slot 12. The outer diameter of the attachment is larger than the lower opening of the end 14 of the conically tapering bone nail, so that the attachment device cannot slip upon introduction, or when pulling the nail.

The bone nail 10 is galvanically connected over the electrodes 28 with the coil 24 and forms one of the electrodes, engaging the bone. The other electrode 36, or the electrodes 36a, 36b, may have galvanic, semiconductive or capacitative connection with the adjacent tissue of the patient. If semiconductive or capacitative contact is desired, the electrodes 36 are suitably coated at the outside with either a thin coating of semiconductor material or with a thin coating of an insulator. A galvanic contact is desirable in tissue poorly supplied with blood, or having few blood vessels. In tissue having better blood supply, a semiconductive contact is desirable. This can be obtained by coating the electrode with a thin layer of aluminum oxide ($Al_2O_3$), biological carbon, calcium phosphate, or the like. If the tissue to be contacted has high blood supply, a capacitative contact may be desirable since rise of current beyond the physiologically compatible value of about $100\mu$ amperes is prevented. Galvanic contact, due to the high conductivity of tissue well supplied with blood might result in an excessive current flow.

Embodiment of FIG. 6

The attachment has four tissue electrodes 36a, 36b, 36c, 36d. The projection 30 which carries these electrodes is subdivided into four parts 30a, 30b, 30c, 30d (see view A). The body 22 is constricted between the respective projections, as seen at 40a, 40b, 40c. As seen in the electrical connection of FIG. 6, view B, one end of the coil 24 is connected to the electrode 28 which is used to connect the entire unit to the bone nail 10. The electrodes 28 are identical to those described in connection with FIGS. 2 and 3. The soft-tissue electrodes 36a to 36d are connected to winding terminals of the coil 24 which have increasingly longer distances from the end of the coil 24 connected to the electrodes 28.

The attachment in accordance with FIG. 6 can be fitted to bone nails of any length by cutting or trimming the body 22 at any one of the constrictions 40a, 40b, 40c, which function as break point, so that the extent of contact of the tissue electrodes can be matched to the extent of the region of the fracture which is to be subjected to an electrical current. The soft-tissue electrodes 36b to 36d are connected to the coil 24 by connecting lines 42, for example in the form of thin foils, which can be readily severed.

Circuit arrangements, with reference to FIGS. 7 and 8

The circuit of FIG. 7 permits application to the electrodes of a-c with a superimposed d-c. As seen, coil 24 is connected in series with a semiconductor rectifier 50 and two voltage divider resistors 52, 54. The tap point 56 of the voltage divider thus has a d-c potential appear thereat. The magnitude will depend on the a-c induced in the coil 24 and the dimension of the voltage divider resistors 52, 54. The tap 56 is additionally connected by a capacitor 58 to the junction of the diode rectifier 50 and the coil 24 so that the d-c voltage appearing at the tap 56 is superimposed on the a-c supplied by the coil 24. The tap 56 and the terminal 60 of the coil 24 are connected, respectively, to the electrodes 36, 28 (FIGS. 2, 3; 4–6) so that the bone nail is negative with respect to the soft-tissue electrode. The diode 50 preferably is a miniature semiconductor diode with low threshold voltage, for example of 50 mV. The circuit is suitably so dimensioned that the d-c component is about 20% of the peak amplitude of the a-c voltage; in a preferred form, the d-c component is approximately 10% of the peak amplitude of the a-c voltage which may be about 1 V or possibly even higher.

The embodiment of FIG. 8 is a modification of the circuit for an insert in accordance with FIG. 4, in which the a-c is applied to the junction 56 from a tap 62 of the coil 24. The capacitor then need not be used. a-c can be applied to the terminal 56 also over a separate winding, for example formed on another layer of winding 24, and connected between terminals 60 and 56.

The rectifier diode 50 is connected to the winding 24 over a conductor loop which, physically, extends into a projecting portion 66 of the body 22, respectively, as schematically indicated in broken lines in FIG. 8. If the surgeon decides that no d-c should be applied, he can cut the projection 66 during the surgical procedure, thus interrupting connection between coil 24 and the rectifier diode 50, so that the applied electric current will be only a-c, without a d-c component.

Embodiment of FIG. 9

The attachment can be used not only with a bone nail, but also with an osteosynthesis plate 70, shown in broken lines in FIG. 9. The attachment 72 has a body 74 made of biologically tissue-compatible material, similar to body 22, in which a receiving coil is located. The receiving coil has been omitted from FIG. 9 for clarity. The body 74 preferably has an approximately rectangular cross section which has a thickness not substantially in excess of that of the plate 70. One or more pairs of knife contact electrodes 76 project from one side of the body 74. Preferably, these contacts 76 are made of springy metal which simultaneously provide electrical connection to the plate 70 as well as ensuring attachment of the body 74 on the plate 70. The electrodes 76, similar to the electrodes 28 of FIGS. 1–6, form electrical contact between the coil in the body 74 and the plate 70. An additional spring electrode 28' may be provided which, similar to the electrodes 28 of the embodiment of FIGS. 2 and 3 is bowed or bulged outwardly and set in at an edge of the body 74, to bear against the edge of plate 70 when the attachment 72 is associated with the plate 70. The body 74 has additional strip-like springy projections 78, made of plastic, and for example molded integrally on the body 74. The projections 78 carry connection arrangements 80, connected over the projections 78 by electrical leads embedded therein with the coil 24 in body 74, similar to the electrodes 36a to 36d, FIG. 6. The connection arrangements 80 permit connection of the coil 74 to bone screws, not shown. The bone screws are insulated with respect to the plate 70 and, simultaneously, form electrodes and attach the plate 70 to the bone. These screws may be constructed as described in the aforementioned U.S. Pat. No. 3,918,440. Projections 78 which are not needed can be trimmed. The projections may have different lengths, as shown, and be so constructed that the location of the connection arrangements 80 corresponds to the position or distribution of the holes in a standard osteosynthesis plate.

Embodiment of FIG. 10

Two bodies 74a, 74b, each one similar to body 74 (FIG. 9) and each one having a coil 24a, 24b, are located at opposite sides of a plate 70 (not shown, and omitted for clarity). The lower ends of the receiving coils have electrodes 76 and, if desired, electrodes 78 attached thereto, similar to the illustration of FIG. 9, and also omitted from FIG. 10. The sense of winding or connection of the coils 24a, 24b may be the same, or opposite, so that the terminals 80 of facing projections 78 will either carry the same, or different voltage levels. The two bodies 74a, 74b are connected at their ends—only one is shown—by a spring 82 made of plastic material so that the attachment arrangement can be used for plates of different widths.

Embodiment of FIG. 11

The projections 78', which carry the connection arrangement 80, are preferably so constructed that they are made of two elastic, oppositely bowed strips, made of plastic. In quiescent state, they are widely bent—see FIG. 11, view A. The strips act like a spring so that the position of the connection arrangement 80 can be matched to different distances of the connection openings between the edge of the plate and the openings for the bone screws themselves, with which the contact elements 80 are to be connected.

Use and application

When using the attachment in accordance with FIGS. 9 and 10, the bone plate 70 is first secured to the bone to be joined, or set. Insulated bone screws having heads which fit the connection arrangement 80 are used at those portions where electrodes are deemed desirable. Thereafter, the attachment body 74, or 74a, 74b, is attached to the plate by sliding it on the longitudinal edge of the plate; the insulated bone screws are then connected with the connection 80 of the projections 78, or 78' (FIG. 11). Those connection elements which are not desired or used are cut off together with the respective projections 78, 78'.

The attachment permits the surgeon to decide during the operation whether healing of a fractured or otherwise injured bone will be promoted by introducing an electrical current to the region of fracture or disease, and if electrodynamic activation of osteosynthesis desirable.

If the attachment is to be used for an ostesynthesis implantate made of a non-conductive material, such as ceramic, then the electrode which is designed for contact with the implantate is, instead, contacted with a large-area electrode foil, or sheet electrode which, preferably, is in contact with the soft tissue of the patient, preferably with the soft tissue immediately adjacent to the bone which is to heal. When using the embodiment in accordance with FIGS. 4 or 5, one of the electrodes 36a, 36b . . . . can be used as the tissue counter electrode.

The body 22, or 72, respectively, may also be made of metal and, for example, may include a housing made of a tissue-compatible material such as a cobalt-chrome alloy, chrome-nickel manganese steel; titanium, or the like. The body can then be used directly as the electrode for connection to a metallic osteosynthesis implantate, or as a large-area, soft-tissue electrode. The other electrodes are then suitably insulated from this conductive body, for example by a thin coating of biologically compatible plastic.

Various changes and modifications may be made, and features described in connection with any one of the embodiments may be used with any of the others, within the scope of the inventive concept.

I claim:

1. An attachment for converting an osteosynthesis plate (70) into an electrified osteosynthesis plate,
   in which the osteosynthesis plate is adapted for attachment to a bone of a patient by at least one metallic bone screw,
   said attachment (72) comprising
   at least one support body formed as an elongated, strip-like element of a dimension adapted to fit adjacent a surface of said plate;
   an induction pick-up coil (24, 24a, 24b) located in the body and having at least two terminals;
   a plurality of members (76, 78) supported by and protruding from the body forming projecting fingers adapted to grip around another surface of said plate to mechanically secure the body (74) to the plate (70);
   a connecting device (80) for electrical and mechanical connection to the bone screw, insulated with respect to the plate, formed on at least one of said fingers (78), said connecting device being electrically connected to at least one of said terminals, the bone screw serving as a tissue electrode for electrically connecting the one terminal to the tissue of the patient;
   and means for electrically connecting another of the at least two terminals to the tissue of the patient.

2. Attachment according to claim 1, wherein the elongated body (74) is dimensioned to fit laterally along an edge of the osteosynthesis plate (70), the projecting fingers (76, 78) extending from said body (74) to fit around both flat sides of the plate (70);
   and some of said fingers (78) include a connecting device and an electrical connection to the coil (24; 24a; 24b) from the connecting device 80.

3. Attachment according to claim 2, wherein two elongated elements (74a, 74b) are provided together forming said support body, one, each, adapted to fit against a lateral edge of said plate;
   and resilient connecting means (82) are provided for connecting said two elements together.

4. Attachment according to claim 3 wherein the support body (74) comprises electrically insulating material.

5. Attachment according to claim 2, wherein at least some of said fingers comprise resiliently elongatable elements (78').

6. Attachment according to claim 2, wherein some of the protruding members forming the fingers are metallic and some have an insulating surface;
   the fingers are positioned at spaced locations along said body (74);
   and wherein the metallic fingers extend from said body at a position adapted to fit adjacent one surface of said plate;

the insulated fingers extend from said body at a position adapted to fit over an opposite, parallel surface of said plate; and wherein the metal fingers and the insulating fingers are spaced from each other essentially by the thickness of the plate, and are in essential alignment with each other to provide for engaging contact by the metal fingers with one major surface of the plate and by the insulated fingers against the other major surface of the plate, said metal and insulated fingers cooperating to grip the plate therebetween.

7. Attachment according to claim 6 wherein the support body (74) comprises electrically insulating material.

8. Attachment according to claim 2 wherein the suppport body (74) comprises electrically insulating material.

9. Attachment according to claim 1, wherein the plate has a plurality of bone screw receiving openings;

and some of said fingers (78) include a connecting device and an electrical connection to said coil (24; 24a; 24b) from the connecting device (80) for connection to a bone screw passing through said screw receiving openings.

10. Attachment according to claim 9 wherein the support body (74) comprises electrically insulating material.

11. Attachment according to claim 1, wherein at least some of the fingers (76) are electrically connected to the coil and have a conductive surface at the side facing said plate, and are adapted for surface engagement with said plate (70) and forming said means for electrically connecting another of the at least two terminals to the tissue of the patient;

and said plate has a metallized surface in the region of surface engagement by said at least some fingers to permit establishment of electrical connection between said at least some fingers and said plate.

12. Attachment according to claim 11 wherein the support body (74) comprises electrically insulating material.

13. An attachment according to claim 1 wherein the means for electrically connecting said another of the at least two terminals comprises a metal protruding member (76) adapted to make electrical contact with an electrically conductive surface of said plate which thereby serves as a second tissue electrode.

14. An attachment according to claim 1 wherein the means for electrically connecting said another of the at least two terminals comprises a second connecting device for electrical and mechanical connection to a second bone screw insulated against the first mentioned bone screw, said second bone screw thereby serving as a second tissue electrode.

15. An attachment according to claim 1, in which there are at least three terminals on the induction pick-up coil, one of the terminals being connected to at least one of said protruding members (76), said at least one member being metallic and adapted to make electrical contact with an electrically conductive surface of said plate which thereby forms the means for electrically connecting another of the at least two terminals to the tissue of the patient, and serves as a tissue electrode; and wherein the remaining terminals are provided with respective connecting devices for electrical and mechanical connection to respective bone screws, insulated with respect to the plate and each other.

16. Attachment according to claim 1 wherein said body is formed in two parallel portions (74a, 74b), the protruding members on each body being directed generally towards the protruding members of the other body portion;

and at least one resilient connecting member (82) mechanically connecting the parallel portions together, to permit mounting said parallel body portions on opposite edges of a rectangular plate.

17. Attachment according to claim 1 wherein the support body (74) comprises electrically insulating material.

18. Attachment according to claim 1 wherein the support body (74) comprises electrically conductive material and is electrically connected to said another of the at least two terminals to form an electrical connection to the tissue of the patient.

* * * * *